United States Patent
Schroeder (10) Patent No.: US 9,816,967 B2
(45) Date of Patent: Nov. 14, 2017

(54) SYSTEM AND METHOD FOR MACHINE AXIS COORDINATION FOR ULTRASONIC INSPECTION

(71) Applicant: Spirit AeroSystems, Inc., Wichita, KS (US)

(72) Inventor: Matthew Ryan Schroeder, Wichita, KS (US)

(73) Assignee: Spirit AeroSystems, Inc., Wichia, KS (US)

( * ) Notice: Subject to any disclaimer, the term of this patent is extended or adjusted under 35 U.S.C. 154(b) by 303 days.

(21) Appl. No.: 14/717,592

(22) Filed: May 20, 2015

(65) Prior Publication Data

US 2016/0341700 A1 Nov. 24, 2016

(51) Int. Cl.
*G01N 29/04* (2006.01)
*G01N 29/265* (2006.01)
*G01N 29/22* (2006.01)

(52) U.S. Cl.
CPC ......... *G01N 29/225* (2013.01); *G01N 29/043* (2013.01); *G01N 29/265* (2013.01); *G01N 2291/023* (2013.01); *G01N 2291/106* (2013.01); *G01N 2291/2694* (2013.01)

(58) Field of Classification Search
CPC .. G01N 29/225; G01N 29/265; G01N 29/043; G01N 2291/2694; G01N 2291/106; G01N 2291/023
USPC .......................................................... 73/487
See application file for complete search history.

(56) References Cited

U.S. PATENT DOCUMENTS

| | | | | |
|---|---|---|---|---|
| 4,669,312 A * | 6/1987 | Maurer | ............. | G01N 29/0618 73/599 |
| 7,114,406 B2 * | 10/2006 | Wright | .................... | B25J 15/04 73/866.5 |
| 8,644,964 B2 * | 2/2014 | Hendron | ................ | G05B 11/01 700/20 |
| 8,925,184 B2 * | 1/2015 | Condliff | ................... | B21J 15/02 29/715 |
| 9,017,326 B2 * | 4/2015 | DiNardo | ........ | A61B 17/320092 606/171 |
| 9,334,066 B2 * | 5/2016 | Tapia | .................... | B64F 5/0045 |
| 9,481,082 B1 * | 11/2016 | Hafenrichter | ............. | B25J 5/02 |

(Continued)

FOREIGN PATENT DOCUMENTS

| | | | |
|---|---|---|---|
| CA | 2261505 | * | 8/2000 |
| WO | WO9837819 | * | 9/1998 |

*Primary Examiner* — J M Saint Surin
(74) *Attorney, Agent, or Firm* — Hovey Williams, LLP (57) ABSTRACT

A through-transmission ultrasonic (TTU) inspection system for ultrasonic inspection of a part and for determining alignment calibration data for increased alignment accuracy. The TTU inspection system may include first and second end effectors located on opposite sides of the part, each having at least one transducer for transmitting or receiving ultrasonic or sound waves through the part. The TTU inspection system may also include actuators and a system controller. The system controller may command the actuators to actuate the first end effector according to one or more scanning patterns, while the transducers send and/or receive signals to or from each other through the part. The system controller may use signal strength measurements received along these scanning patterns to determine alignment calibration data for applying to the first end effector and/or its associated actuators.

20 Claims, 6 Drawing Sheets

(56) References Cited

U.S. PATENT DOCUMENTS

| | | | | |
|---|---|---|---|---|
| 2007/0137302 A1* | 6/2007 | Fetzer | ................ | G01N 29/225 |
| | | | | 73/649 |
| 2009/0030351 A1* | 1/2009 | Wiener | .......... | A61B 17/320068 |
| | | | | 601/2 |
| 2013/0145850 A1* | 6/2013 | Lute, Jr. | ............... | G01N 29/043 |
| | | | | 73/619 |
| 2014/0341700 A1* | 11/2014 | Vopat | ................ | B25J 15/0052 |
| | | | | 414/805 |
| 2016/0334374 A1* | 11/2016 | Koerner | ............... | G01N 29/28 |

* cited by examiner

SYSTEM AND METHOD FOR MACHINE AXIS COORDINATION FOR ULTRASONIC INSPECTION

BACKGROUND

Commercial airplanes and components thereof are increasingly manufactured from composite materials that may require ultrasonic inspection to determine part integrity. In order to perform an ultrasonic inspection, a transducer that transmits and/or receives sound waves must be acoustically coupled to the part. Water or some other liquid is typically disposed between the transducer and the part to be inspected to provide a medium through which sound waves can travel.

Inspection may be performed from one side (i.e., pulse-echo inspections) or from two sides, referred to herein as the through-transmission (TTU) method. The one side, pulse-echo inspection method is not effective on honeycomb core sandwich panels, so the TTU method is needed to inspect such structures. In addition, the TTU method may provide a more detailed assessment of the condition of a part than other methods. For example, TTU inspection can be used to quantify the amount of porosity present in a composite laminate. A TTU inspection is performed by transmitting sound waves into one side of the part and receiving the sound waves on the opposite side of the part using two transducers coupled to the part simultaneously and on opposite sides.

To insure accurate results, the TTU method requires alignment of transducers sending and receiving the ultrasonic waves. Some prior art methods exist for aligning these transducers before the part is placed therebetween. However, for large, complex composite parts, it can be difficult to maintain this alignment.

SUMMARY OF THE INVENTION

Embodiments of the present invention solve the above-mentioned problems and provide a distinct advance in the art of aligning ultrasonic inspection transducers on opposing sides of a part to be inspected.

One embodiment of the invention is an ultrasonic inspection system for ultrasonic inspection of a part. The system may include a first end effector, a second end effector, one or more actuators, and a system controller. The first and second end effectors may each have at least one transducer for transmitting or receiving ultrasonic or sound waves through the part. The actuators may receive commands for actuating the first end effector and the second end effector, and the system controller may have a processor for determining alignment calibration data for the first end effector, while the first and second end effectors are located on opposite sides of the part. The system controller may also output command signals to the actuators for actuating the first end effector according to the determined alignment calibration data.

Another embodiment of the invention is a computer-implemented method for properly aligning a through-transmission ultrasonic (TTU) inspection system's first and second end effectors while located on opposite sides of a part to be inspected. The first and second end effectors each include at least one transducer for transmitting and receiving ultrasonic or sound waves through the part. The computer-implemented method may include a step of actuating the first end effector according to a first scanning pattern within a predetermined work envelope, starting at a first location or orientation, while the first end effector transmits or receives ultrasonic or sound waves and the second end effector receives or transmits ultrasonic sound waves at each point along the first scanning pattern. Then, the method may include the steps of determining a best alignment position A based on a location or orientation of the first end effector at which signal strength received or sent by the second end effector was strongest along the first scanning pattern that started at the first location or orientation, then moving the first end effector and the second end effector to a second starting location or orientation on opposite sides of the part. Next, the method may include the steps of actuating the first end effector according to a first scanning pattern within the predetermined work envelope, starting at the second location or orientation, while the first end effector transmits or receives ultrasonic or sound waves and the second end effector receives or transmits ultrasonic sound waves at each point along the first scanning pattern, then determining a best alignment position B based on a location or orientation of the first end effector at which signal strength received or sent by the second end effector was strongest along the first scanning pattern that started at the second location or orientation. Finally, the method may include the steps of computing a transformation using best alignment position A and best alignment position B throughout the predetermined work envelope, and applying the transformation as alignment calibration data for the first end effector to maintain accurate alignment of the first end effector and the second end effector while conducting ultrasonic inspection of the part.

Another embodiment of the invention is a physical, non-transitory computer-readable medium with an executable program stored thereon for properly aligning first and second end effectors of a through-transmission ultrasonic (TTU) inspection system while the first and second end effectors are located on opposite sides of a part to be inspected. The first and second end effectors each include at least one transducer for transmitting or receiving ultrasonic or sound waves through the part. The program may include a code segment for commanding actuation of the first end effector according to a first scanning pattern within a predetermined work envelope, starting at a first location or orientation, while the first end effector transmits or receives ultrasonic or sound waves and the second end effector remains stationary and receives or transmits ultrasonic sound waves at each point visited by the first end effector along the first scanning pattern, and a code segment for determining a best alignment position A based on a location or orientation of the first end effector at which signal strength received or sent by the second end effector was strongest along the first scanning pattern that started at the first location or orientation. The program may also include a code segment for moving the first end effector and the second end effector to a second starting location or orientation on opposite sides of the part, and a code segment for commanding actuation of the first end effector according to a first scanning pattern within the predetermined work envelope, starting at the second location or orientation, while the first end effector transmits or receives ultrasonic or sound waves and the second end effector remains stationary and receives or transmits ultrasonic sound waves at each point visited by the first end effector along the first scanning pattern. Next, the program may include a code segment for determining a best alignment position B based on a location or orientation of the first end effector at which signal strength received or sent by the second end effector was strongest along the first scanning pattern that started at the second location or orientation. Then, the program may include a code segment for computing a transformation using best alignment position A and best alignment position B throughout the predetermined work envelope and a code segment for applying the transformation as alignment calibration data for the first end effector, or actuators associated with the first end effector, to maintain accurate alignment of the first end effector and the second end effector while conducting ultrasonic inspection of the part.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the current invention will be apparent from the following detailed description of the embodiments and the accompanying drawing figures.

BRIEF DESCRIPTION OF THE DRAWING FIGURES

Embodiments of the current invention are described in detail below with reference to the attached drawing figures, wherein.

The drawing figures do not limit the current invention to the specific embodiments disclosed and described herein. The drawings are not necessarily to scale, emphasis instead being placed upon clearly illustrating the principles of the invention.

DETAILED DESCRIPTION OF THE EMBODIMENTS

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the current invention. The following detailed description is, therefore, not to be taken in a limiting sense. The scope of the current invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

Figure 1:
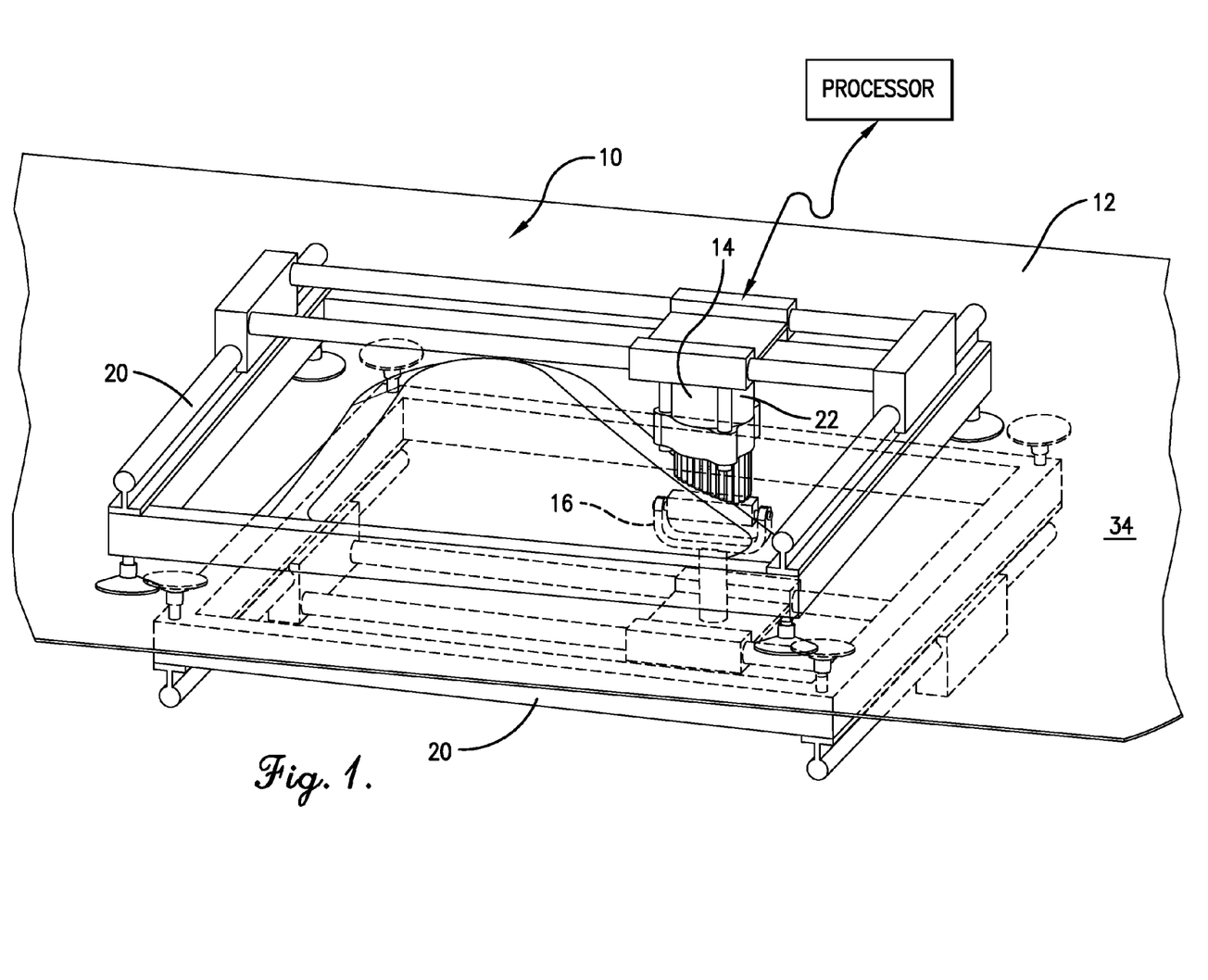
FIG. 1 is a top perspective view of a through-transmission ultrasonic (TTU) inspection system with two ultrasonic end effectors, position actuators, and a system controller constructed according to embodiments of the present invention.
Figure 2:
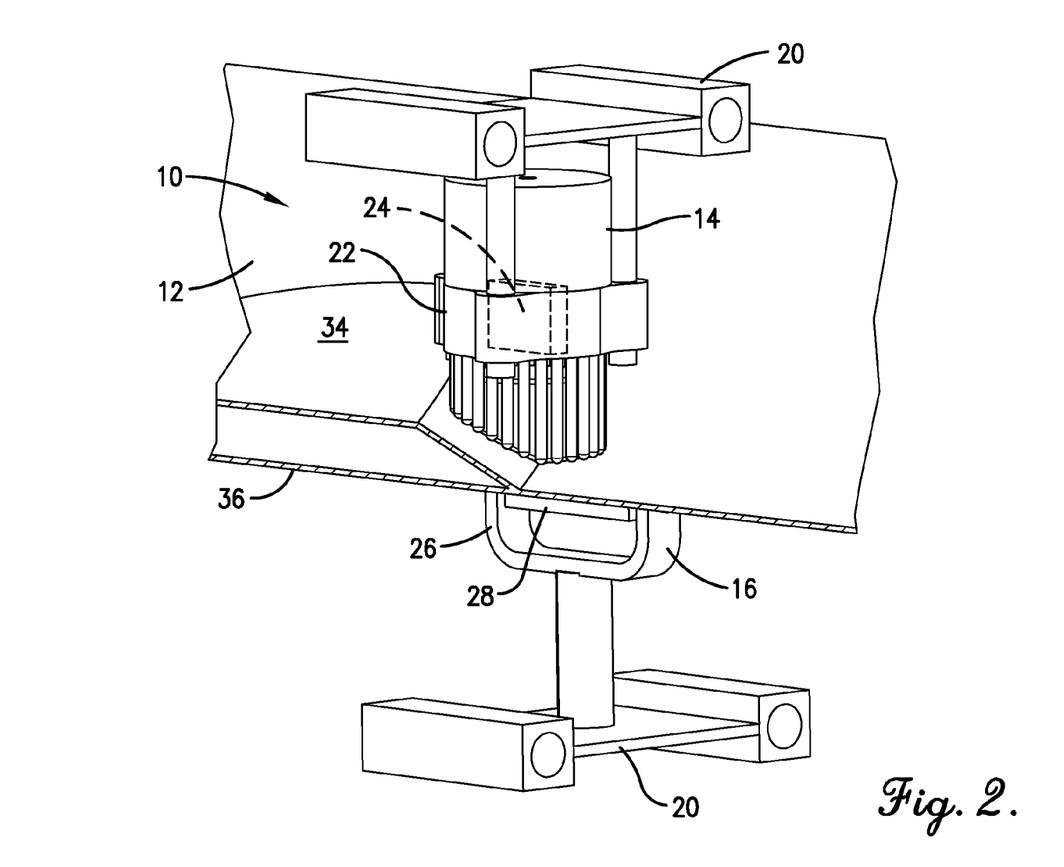
FIG. 2 is a perspective view in partial cross-section of the TTU inspection system of FIG. 1, with the ultrasonic end effectors in misalignment.
Figure 3:
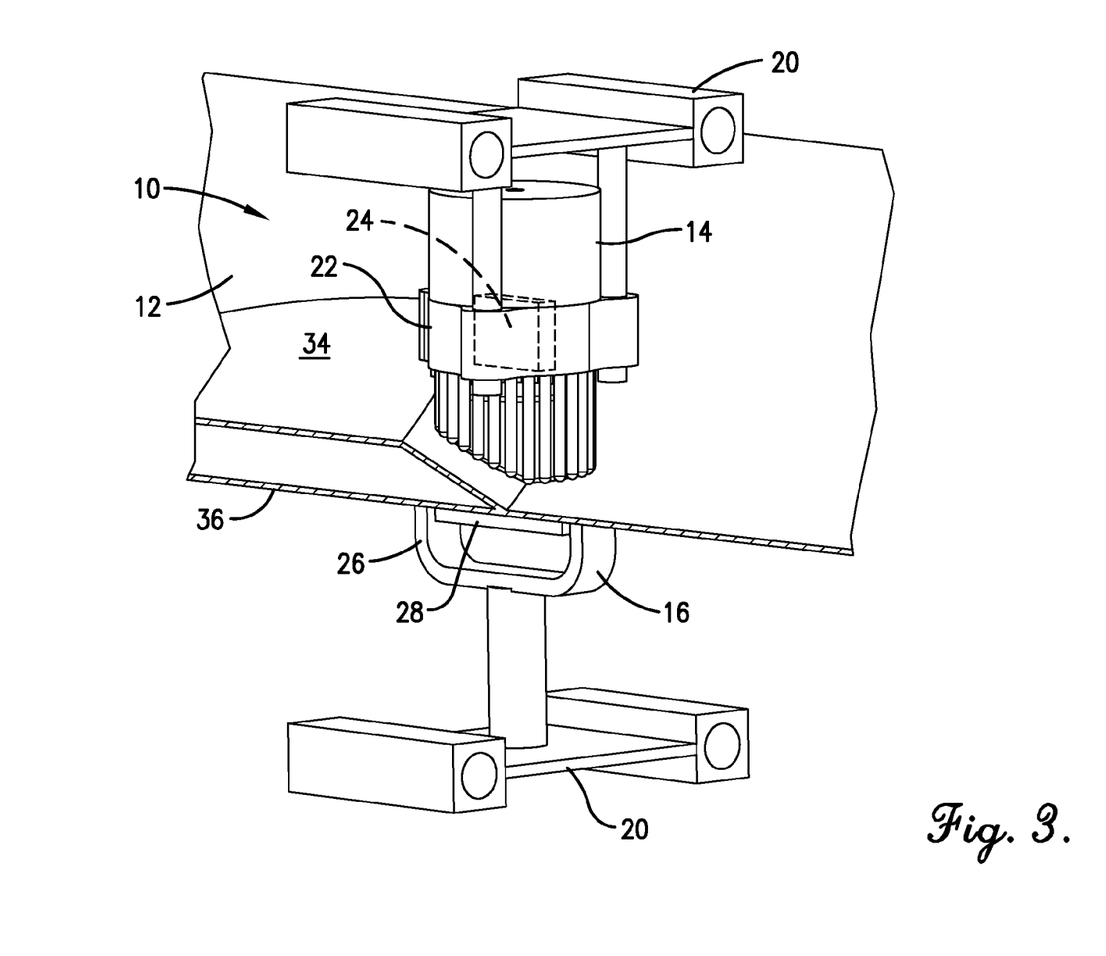
FIG. 3 is a perspective view in partial cross-section of the TTU inspection system of FIG. 1, with the ultrasonic end effectors in alignment.

A through-transmission ultrasonic (TTU) inspection system 10 constructed in accordance with embodiments of the present invention is illustrated in FIGS. 1-3. The system 10 is configured for ultrasonic inspection of a part 12. The part 12 may be any component requiring ultrasonic inspection, such as an aircraft component, nacelle wall, honeycomb panel, and the like. The part may have a first surface 34 and a second surface 36 opposite of the first surface 34. The system 10 broadly comprises a first end effector 14, a second end effector 16, a system controller 18, and a plurality of actuation and support components 20.

As illustrated in FIGS. 2 and 3, the first end effector 14 may comprise a first housing 22 and a first transducer 24 fixed to the first housing 22. Likewise, the second end effector 16 may comprise a second housing 26 and a second transducer 28 fixed to the second housing 26, as illustrated in FIG. 2. The first and second transducers 24,28 may each comprise one or more transducers configured to transmit and/or receive sound waves or ultrasonic waves to and from each other. The transducers 24,28 may include linear arrays of transducers arranged in any configuration, such as a plurality of rows and/or columns of transducers arranged into a square or rectangular pattern.

The first and/or the second end effector 14,16 may be an adaptable end effector as described in U.S. application Ser. No. 14/711,419, filed May 13, 2015, titled "Ultrasonic Inspection End Effector," incorporated by reference herein in its entirety. Specifically, in some embodiments of the invention, both the first and second end effectors 14,16 may be adaptable end effectors. In other embodiments of the invention, only the first or second end effector 14,16 may be an adaptable end effector. In still other embodiments of the invention, both the first and second end effectors 14,16 may be traditional end effectors and/or transducers known in the art of TTU testing.

In some embodiments of the invention, the system controller 18 may comprise a processor and/or computer-readable memory residing thereon or communicably coupled with the processor and may be configured for performing one or more of the method steps described herein. For example, the system controller 18 may include any computer and/or server, such as a desktop computer, a laptop computer, a tablet, a mobile phone, or any other computing device having a data processor and computer-readable memory. The system controller 18 may include or have access to hardware and software for receiving, storing, accessing, and transmitting information. The system controller 18 may also comprise a display, such as a computer monitor, and a user interface, such as a keyboard, mouse, touch screen, or the like for allowing an operator thereof to send and receive information to and from the end effectors 14,16 and/or the actuation and support components 20.

In some embodiments of the invention, the system controller 18 may further include and/or be communicably coupled with one or more servers (not shown) running Windows; LAMP (Linux, Apache HTTP server, MySQL, and PHP/Perl/Python); Java; AJAX; NT; Novel Netware; Unix; or any other software system. The system controller 18 may also include conventional web hosting operating software, searching algorithms, an Internet connection, and may be assigned a URL and corresponding domain name so that it can be accessed via the Internet in a conventional manner.

The computer-readable memory of the system controller 18 may include any data storage device or computer-readable medium, as described herein. In some embodiments of the invention, some or all of the computer-readable memory may be located remotely from the processor. One or more computer programs may be stored in or on the computer-readable medium and may be configured for being executed by the processor. The computer programs may comprise computer code or listings of executable instructions for implementing logical functions in the processor and/or other devices communicably coupled therewith and can be embodied in any non-transitory computer-readable medium for use by or in connection with an instruction execution system, apparatus, or device, such as a computer-based system, processor-containing system, or other system that can fetch the instructions from the instruction execution system, apparatus, or device, and execute the instructions. In the context of this application, a "computer-readable medium" can be any non-transitory means that can contain, store, or communicate the programs. The computer-readable medium can be, for example, but not limited to, an electronic, magnetic, optical, electro-magnetic, infrared, or semi-conductor system, apparatus, or device. More specific, although not inclusive, examples of the computer-readable medium would include the following: an electrical connection having one or more wires, a portable computer diskette, a random access memory (RAM), a read-only memory (ROM), an erasable, programmable, read-only memory (EPROM or Flash memory), an optical fiber, and a portable compact disk read-only memory (CDROM).

The system controller 18 may be communicably coupled with the first and second end effectors 14,16 and/or their transducers 24,28, such that signals received by the transducers 24,28 may be communicated to the system controller 18 during testing of the part 12 and/or alignment/calibration of the transducers 24,28, as later described herein. The system controller 18 may also be communicably coupled with various actuation and support components 20, such as actuators configured for moving the end effectors 14,16 relative to each other and/or relative to the part 12.

In some embodiments of the invention, the system controller 18 may be programmed and/or configured to control at least some of the actuation and support components 20. In some embodiments of the invention, manual actuation of the first and/or second end effectors 14,16 by a user or operator may also be allowed. The system controller 18 may also be configured to send and receive data to and from the end effectors 14,16. For example, ultrasonic waves received by either the end effectors 14,16 by the other of the end effectors 16,14 may be transmitted through wired or wireless technology to the system controller's processor and/or associated memory, databases, cloud storage devices, computer-readable medium, and the like.

The actuation and support components 20, as illustrated in FIG. 1, may be configured for actuating the first and second end effectors 14,16 relative to the part 12. For example, the actuation and support components 20 may comprise rails, actuators, motors, controllers, and various electrical and communication elements for properly locating the first and second end effectors 14,16 relative to the first surface 34 of the part 12 and the second surface 36 of the part 12. In some embodiments of the invention, at least some of the actuation and support components 20, referred to herein as fixed support components, may be configured to be fixed relative to the part, and the first and/or second housings 22,26 may be movable and/or actuatable relative to the fixed support components.

A method for calibrating alignment of end effectors or transducers of the TTU inspection system 10 will now be described. The method may include placing the end effectors 14,16 on the opposing surfaces 34,36 of the part 12 at a first location within a predefined work envelope, and moving the first end effector 14 according to a first scanning pattern while sending and/or receiving ultrasonic waves to or from the second end effector 18. Based on the readings received during completion of the first scanning pattern starting at the first location, the system controller 18 may determine a position A for the first end effector 14 at which the greatest signal strength was received. Next, both the end effectors 14,16 may be moved to a second location within the predefined work envelope and the first end effector may be moved according to the first scanning pattern or any other selected scanning pattern while sending and/or receiving ultrasonic waves to or from the second end effector 18. Based on the readings received during completion of this scanning pattern starting at the second location, the system controller 18 may determine a position B for the first end effector 14 at which the greatest signal strength was received. These steps may be repeated a plurality of times for a plurality of locations within the work envelope, and the resulting positions (i.e., A, B, etc.) at which the greatest signal strength was received may be used by the processor of the system controller 18 to compute a transformation applied to maintain alignment of the first end effector 14 using a best fit or direct transformation, depending on the number of points measured and desired accuracy. This essentially customizes alignment calibration for the end effectors 14,16 specific to location within the predefined work envelope.

Figure 4:
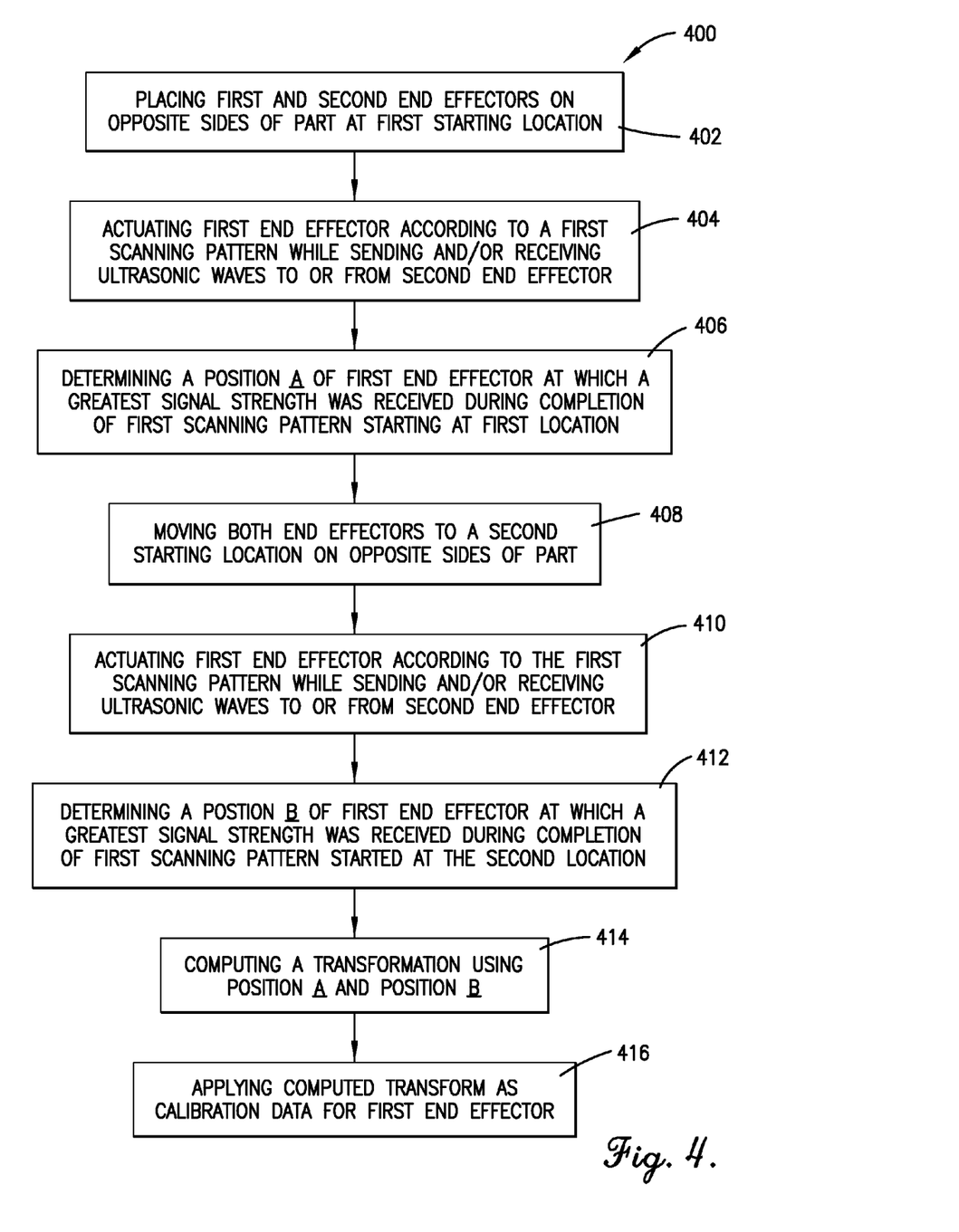
FIG. 4 is a flow chart illustrating a method of accurately aligning the ultrasonic end effectors of FIG. 1 through a part to be tested in accordance with embodiments of the present invention.
Figure 5:
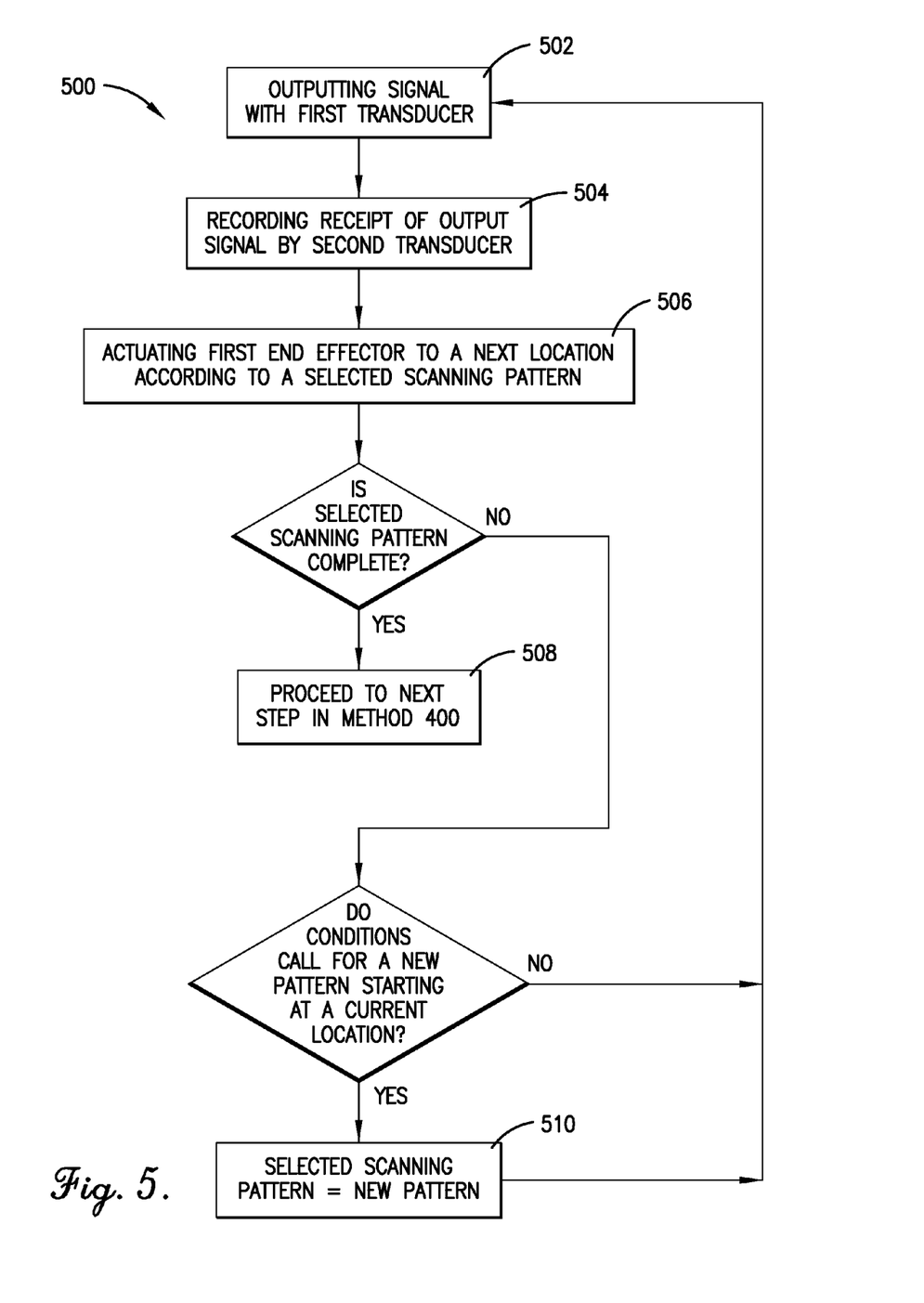
FIG. 5 is a flow chart illustrating execution of a scanning pattern with a first end effector of the TTU inspection system in accordance with embodiments of the invention.
Figure 6:
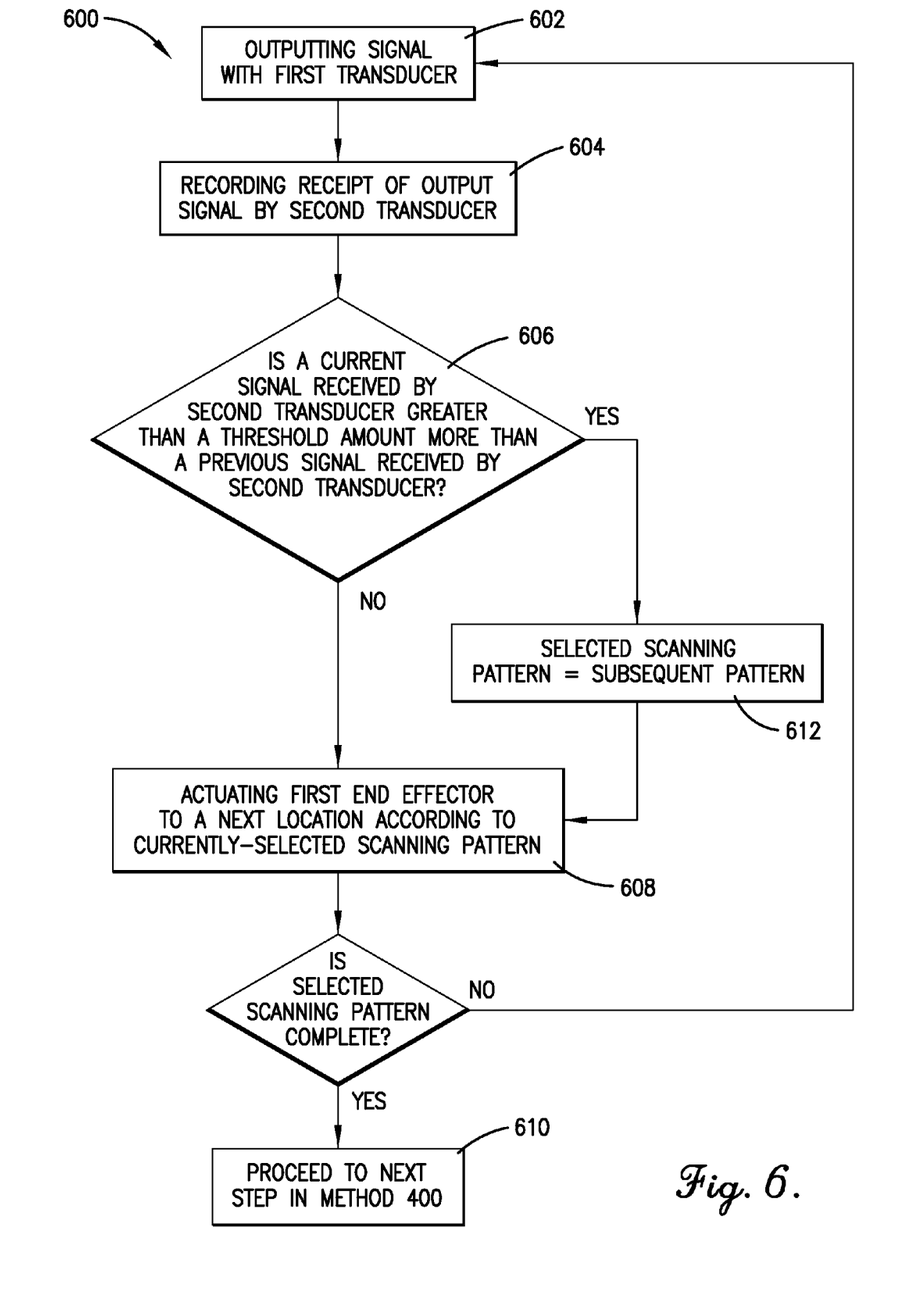
FIG. 6 is a flow chart illustrating execution of a plurality of scanning patterns with the first end effector of the TTU inspection system in accordance with embodiments of the invention.

Method steps for TTU inspection transducer alignment will now be described in more detail, in accordance with various embodiments of the present invention. The steps of the methods 400, 500, and 600 may be performed in the order as shown in FIGS. 4, 5, and 6, respectively, or they may be performed in a different order. Furthermore, some steps may be performed concurrently as opposed to sequentially. In addition, some steps may not be performed. One or more of the steps may represent computer program modules or code segments executable by the processor of the system controller 18 described above.

The method 400 may include a step of placing the end effectors 14,16 on opposite sides (e.g., the opposing surfaces 34,36) of the part 12, as depicted in block 402. In this initial step, a user may align the end effectors 14,16 with each other as closely as possible. For example, the end effectors 14,16 may each begin at a best guess alignment location in relationship to each of their own frames of reference. However, even without initial manual alignment efforts, the method described herein may still automatically determine proper alignment positions and orientations for the end effectors. At least one of the end effectors 14,16 may be fixed to or relative to the part 12 during this initial step. Likewise, the actuation and support elements 20 associated with each of the end effectors may be fixed to or relative to the part 12. Note that the one of the end effectors 14,16 that moves during the alignment method 400 described herein may be either sending ultrasonic signals or receiving ultrasonic signals without departing from the scope of the invention.

Once the end effectors 14,16 are placed in their initial positions relative to the part 12, the method 400 may include actuating the first end effector 14 according to a first scanning pattern while sending and/or receiving ultrasonic waves to or from the second end effector 18, as depicted in block 404. Specifically, FIG. 5 illustrates a method 500 of actuating the first end effector according to a scanning pattern, as described herein. The method 500 may include the steps of outputting a signal with the first transducer 24, as depicted in block 502, recording receipt of the output signal by the second transducer 28, as depicted in block 504, then actuating the first end effector to a next location according to a selected scanning pattern, as depicted in block 506. These steps 502-506 are then repeated until the selected scanning pattern is complete, as depicted in block 508, or the processor determines that a new pattern should begin starting at a current location, as depicted in block 510 and described further below.

The output signal in block 502 may be ultrasonic or sound waves output with the transducer 24 of the first end effector 14. This output signal may then flow through a coupling medium, through the part 12, and then through another coupling medium to the transducer 28 of the second end effector 16. Additionally or alternatively, the output signal in block 502 may be ultrasonic or sound waves output with the transducer 28 and received with the transducer 24 after being transmitted through the coupling medium and the part 12. The signals received by the transducers 24,28 of the first and/or second end effectors 14,16 may be analyzed by the system controller 18 to determine and/or store signal strength. Signal strength may be measured and stored using any methods known in the art.

The scanning patterns described herein may involve any pattern including any plurality of locations within the predetermined work envelope and/or any plurality of angles or orientations. For example, rotation of an end effector may be required to achieve a proper co-linear alignment of rectangular linear arrays of transducers. That is, even if the end effectors 14,16 are centered at an identical point on the part 12, if their respective linear arrays are aligned perpendicular with each other, maximum signal strength may not be achieved. Therefore, in some embodiments of the invention, at least one of the scanning patterns described herein may include progressive rotation of the first end effector. Likewise, due to curvatures or other variations in the part 12, a scanning pattern which rotates angles of the end effectors 14,16 in directions toward and away from the part 12 may also be used in some applications of the invention.

Returning to FIG. 4, the method 400 may then include a step of determining a position A for the first end effector 14 at which the greatest signal strength was received, as depicted in block 406, based on the readings received during completion of the first scanning pattern starting at the first location, as performed in step 404. This position A may be an absolute greatest signal strength or may be an average or center point of the highest signal strengths received. For example, a position for the first end effector 14 that corresponds to a best alignment (i.e., greatest signal strength) between the transducers 24,28 may be calculated as a center of mass type equation using a weighted average of signal strengths. The position A may also be recorded via the processor in the computer-readable memory associated with the system controller 18. In some embodiments of the invention, if none of the signal strengths obtained along the scanning pattern exceed a pre-set minimum threshold, the data may be discarded and the operation may be tried again from a different starting location.

The method 400 may further include a step of moving both of the end effectors 14,16 to a second location within the predefined work envelope, as depicted in block 408. The second location may be at any location within the predefined work envelope, but may typically be a relatively large distance away from the first for greater accuracy (e.g., diagonally-opposing corners of the work envelope). As with the first location, the second location may be a best guess at alignment between the end effectors 14,16. However, in some embodiments of the invention, a translation from the last starting location (e.g., the first location used in block 404) to the best alignment (e.g., position A) may be applied to command signals, output from the system controller 18 to associated actuators, for actuating the first end effector 14. This translation may be an offset to improve accuracy of a starting point for the subsequent starting location (e.g., the second location used in block 408).

The method 400 may then include actuating the first end effector 14 according to the first scanning pattern or any other selected scanning pattern, starting from the second position, while sending and/or receiving ultrasonic waves to or from the second end effector 16, as depicted in block 410. Again, actuating the first end effector 14 according to a selected pattern while sending and/or receiving ultrasonic waves may be accomplished using the method 500 depicted in FIG. 5 and described above.

Next, the method 400 may include a step of determining a position B for the first end effector 14 at which the greatest signal strength was received, as depicted in block 412, based on the readings received during completion of the scanning pattern started at the second location. As described above for position A, position B may also be an absolute greatest signal strength or may be an average or center point of the highest signal strengths received.

Although only two starting points within the preselected work envelope and two best alignment positions (position A and position B) are illustrated in FIG. 4, please note that any of steps 402-412 may be repeated a plurality of times for a plurality of starting locations within the work envelope, thus determining subsequent locations at which the greatest signal strength was received for that new starting location. The number of points measured may depend on desired accuracy as well as time constraints.

Furthermore, although the exemplary method 400 described herein describes the first end effector 14 being actuated according to the selected scanning patterns for both position A and position B, it is possible that the second end effector 16 could be actuated according to the selected scanning patterns for determining position A or for determining position B while the first end effector 14 remains stationary. For example, the first end effector 14 could be stationary while the second end effector 16 is actuated according to the selected scanning pattern(s) for determining position A, and the second end effector 16 could be stationary while the first end effector 14 is actuated according to the selected scanning pattern(s) for determining position B. Alternatively, the second end effector 16 could be stationary while the first end effector 14 is actuated according to the selected scanning pattern(s) for determining position A, and the first end effector 14 could be stationary while the second end effector 16 is actuated according to the selected scanning pattern(s) for determining position B.

Then, the method 400 may include a step of computing a transformation using position A and position B with a best fit or direct transformation throughout the predetermined work envelope, as depicted in block 414, and applying this transform as calibration data for the first end effector 14, as depicted in block 416, to maintain alignment of the first end effector 14 and the second end effector 16 at any locations within the predetermined work envelope while conducting TTU testing of the part 12 with the TTU inspection system 10. In embodiments of the invention where more than two starting positions are used for determining best alignment positions, all of the subsequent best alignment positions determined may also be used along with position A and position B to calculate the transformation. Which type of transformation is used may depend on how many best alignment positions are determined and a desired accuracy for a given application of the method 400. The end effectors 14,16 are thus aligned and ready to begin TTU inspection of the part at any or all locations within the pre-determined work envelope.

In some alternative embodiments of the invention, method 500 for actuating the first end effector 14 according to a scanning pattern while sending and/or receiving ultrasonic waves to or from the second end effector 18 may be replaced with method 600, as depicted in FIG. 6, which is an iterative process for using progressively tighter and/or more fine-tuned scanning patterns to more quickly and/or more accurately identify the best alignment positions.

The method 600 may include the steps of outputting a signal with the first transducer 24, as depicted in block 602 and recording receipt of the output signal by the second transducer 28, as depicted in block 604. Then the method may include comparing a current signal received by the second transducer 28 with a previous signal received by the second transducer, as depicted in block 606, to determine if signal strength has increased by a threshold amount. For example, the current signal, most-recently recorded in the computer-readable memory, may be compared to a last-recorded signal, recorded at a last-visited location in the scanning pattern) to determine if signal strength has increased by a threshold amount. Alternatively, this comparing step 606 may include determining if the current signal strength exceeds a predetermined threshold signal strength stored in the computer-readable memory.

If signal strength has not increased by the threshold amount or there is no last-recorded signal for comparison (i.e., current location is the starting location), then the method 600 may next include a step of actuating the first end effector to a next location of a selected scanning pattern, as depicted in block 608. For example, the selected scanning pattern may initially be the first scanning pattern, as described above. Then steps 602-606 may be repeated until the selected scanning pattern is complete, as depicted in block 610.

If the signal strength has increased by the threshold amount, or has increased above the specific predetermined threshold signal strength, the method 600 may then include switching the selected scanning pattern to a second scanning pattern or another subsequent scanning pattern starting at a current location, as depicted in block 612. This second scanning pattern or other subsequent scanning patterns may therefore begin from a point of increased signal strength (e.g., a current location at which the signal strength is stronger than signal strength of a last location) and may, for example, be run at a lower speed and/or tighter scanning pattern (e.g., higher resolution) than the first or previous scanning patterns if required by an alignment tolerance for a given application of the methods 400 and/or 600. In some alternative embodiments of the invention, the second scanning pattern may begin after the first scanning pattern is complete and may begin at a point of greatest signal strength from the first scanning pattern. In another alternative embodiment of the invention, the second scanning pattern may begin at a previous location if the current signal has decreased by a threshold amount from the previous signal. After a new scanning pattern is selected, step 608 of actuating one of the end effectors 14,16 to a next location of the selected scanning pattern may be performed.

As with the first scanning pattern, if the second scanning pattern is not yet complete, the method 600 may then repeat steps 602-606 for the second scanning pattern until this pattern ends (as in step 610), another increase in signal strength determines advancing to a third or subsequent scanning pattern (as in step 612), or a desired signal strength is sensed (not shown). In some alternative embodiments of the invention, steps 602-606 may be performed over a pre-set area, until a maximum value of a previous scanning pattern (e.g., a maximum signal strength recorded while moving along the first scanning pattern) exceeds a maximum signal strength recorded in the second scanning pattern or subsequent scanning patterns. Furthermore, in some embodiments of the invention, a pre-determined maximum number of subsequent scanning patterns may be allowed.

Although the invention has been described with reference to the embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. An ultrasonic inspection system for ultrasonic inspection of a part, the system comprising:
   a first end effector having at least one transducer configured to transmit or receive ultrasonic or sound waves through the part; and
   a second end effector having at least one transducer configured to transmit or receive ultrasonic or sound waves through the part;
   actuators configured to receive commands for actuating the first end effector and the second end effector; and
   a system controller comprising a processor configured for determining alignment calibration data for at least one of the first end effector and the second end effector while the first and second end effectors are located on opposite sides of the part, and configured for outputting command signals to the actuators for actuating the at least one of the first end effector and the second end effector according to the determined alignment calibration data,
   wherein the system controller is further configured for sending signals to one of the actuators to actuate the first end effector according to a first scanning pattern within a predetermined work envelope, starting at a first location or orientation, while the first end effector transmits or receives ultrasonic or sound waves and the second end effector receives or transmits ultrasonic sound waves at each point along the first scanning pattern,
   wherein the system controller is further configured to calculate a best alignment position A based on a location or orientation of the first end effector at which signal strength received or sent by the second end effector was strongest along the first scanning pattern that started at the first location or orientation.

2. The system of claim 1, wherein the system controller is further configured for sending signals to one of the actuators to actuate the first end effector according to a first scanning pattern within the predetermined work envelope, starting at a second location or orientation, while the first end effector transmits or receives ultrasonic or sound waves and the second end effector receives or transmits ultrasonic sound waves at each point along the first scanning pattern.

3. The system of claim 2, wherein the system controller is further configured to calculate a best alignment position B based on a location or orientation of the first end effector at which signal strength received or sent by the second end effector was strongest along the first scanning pattern that started at the second location or orientation.

4. The system of claim 3, wherein the system controller is further configured for computing, using best alignment position A and best alignment position B, a transformation throughout the predetermined work envelope and applying this transformation as the alignment calibration data for the first end effector to maintain alignment of the first end effector and the second end effector while conducting ultrasonic inspection of the part.

5. The system of claim 1, further comprising support components configured for fixing the second end effector to the part in estimated alignment with the first end effector at the first location or orientation.

6. The system of claim 1, wherein the system controller is further configured to start a second scanning pattern:
at a current location or orientation if a current signal sent or received by the first end effector at the current location is greater than a threshold amount more than a previous signal sent or received at a previous location or orientation,
at a location or orientation along the first scanning pattern at which signal strength received or sent by the second end effector was strongest, or
at the current location or orientation if the current signal sent or received by the first end effector at the current location exceeds a threshold signal strength.

7. The system of claim 6, wherein the second scanning pattern runs at a lower speed, makes tighter turns, or runs at a higher resolution than the first scanning pattern.

8. A computer-implemented method for properly aligning through-transmission ultrasonic (TTU) inspection system first and second end effectors while located on opposite sides of a part to be inspected, wherein the first and second end effectors each comprise at least one transducer configured to transmit or receive ultrasonic or sound waves through the part, the method comprising the steps of:
actuating the first end effector according to a first scanning pattern within a predetermined work envelope, starting at a first location or orientation, while the first end effector transmits or receives ultrasonic or sound waves and the second end effector receives or transmits ultrasonic sound waves at each point along the first scanning pattern;
determining a best alignment position A based on a location or orientation of the first end effector at which signal strength received or sent by the second end effector was strongest along the first scanning pattern that started at the first location or orientation;
moving the first end effector and the second end effector to a second starting location or orientation on opposite sides of the part;
actuating the first end effector according to a first scanning pattern within the predetermined work envelope, starting at the second location or orientation, while the first end effector transmits or receives ultrasonic or sound waves and the second end effector receives or transmits ultrasonic sound waves at each point along the first scanning pattern;
determining a best alignment position B based on a location or orientation of the first end effector at which signal strength received or sent by the second end effector was strongest along the first scanning pattern that started at the second location or orientation;
computing a transformation using best alignment position A and best alignment position B throughout the predetermined work envelope; and
applying the transformation as alignment calibration data for the first end effector to maintain accurate alignment of the first end effector and the second end effector while conducting ultrasonic inspection of the part.

9. The method of claim 8, further comprising a step of fixing the second end effector to the part in an estimated alignment with the first end effector at the first location or orientation.

10. The computer-implemented method of claim 8, further comprising a step of starting a second scanning pattern:
at a current location or orientation if a current signal sent or received by the first end effector at the current location is greater than a threshold amount more than a previous signal sent or received at a previous location or orientation,
at a location or orientation along the first scanning pattern at which signal strength received or sent by the second end effector was strongest, or
at the current location or orientation if the current signal sent or received by the first end effector at the current location exceeds a threshold signal strength.

11. The computer-implemented method of claim 10, wherein the second scanning pattern runs at a lower speed, makes tighter turns, or runs at a higher resolution than the first scanning pattern.

12. The computer-implemented method of claim 8, further comprising applying a translation to the first end effector at the second location or orientation, wherein the translation is based on the best alignment position A, improving starting position accuracy of the second location or orientation.

13. The computer-implemented method of claim 8, wherein at least one of the best alignment position A and the best alignment position B are calculated as a center of mass type equation or based on a weighted average of signal strengths.

14. A physical, non-transitory computer-readable medium with an executable program stored thereon for properly aligning first and second end effectors of a through-transmission ultrasonic (TTU) inspection system while the first and second end effectors are located on opposite sides of a part to be inspected, wherein the first and second end effectors each comprise at least one transducer configured to transmit or receive ultrasonic or sound waves through the part, the program comprising:
a code segment for commanding actuation of the first end effector according to a first scanning pattern within a predetermined work envelope, starting at a first location or orientation, while the first end effector transmits or receives ultrasonic or sound waves and the second end effector remains stationary and receives or transmits ultrasonic sound waves at each point visited by the first end effector along the first scanning pattern;
a code segment for determining a best alignment position A based on a location or orientation of the first end effector at which signal strength received or sent by the second end effector was strongest along the first scanning pattern that started at the first location or orientation;

a code segment for moving the first end effector and the second end effector to a second starting location or orientation on opposite sides of the part;

a code segment for commanding actuation of the first end effector according to a first scanning pattern within the predetermined work envelope, starting at the second location or orientation, while the first end effector transmits or receives ultrasonic or sound waves and the second end effector remains stationary and receives or transmits ultrasonic sound waves at each point visited by the first end effector along the first scanning pattern;

a code segment for determining a best alignment position B based on a location or orientation of the first end effector at which signal strength received or sent by the second end effector was strongest along the first scanning pattern that started at the second location or orientation;

a code segment for computing a transformation using best alignment position A and best alignment position B throughout the predetermined work envelope; and a code segment for applying the transformation as alignment calibration data for the first end effector, or actuators associated with the first end effector, to maintain accurate alignment of the first end effector and the second end effector while conducting ultrasonic inspection of the part.

15. The program of claim 14, further comprising a code segment for starting a second scanning pattern:
at a current location or orientation if a current signal sent or received by the first end effector at the current location is greater than a threshold amount more than a previous signal sent or received at a previous location or orientation,
at a location or orientation along the first scanning pattern at which signal strength received or sent by the second end effector was strongest, or
at the current location or orientation if the current signal sent or received by the first end effector at the current location exceeds a threshold signal strength.

16. The program of claim 15, wherein the second scanning pattern is programmed to run at a lower speed, make tighter turns, or run at a higher resolution than the first scanning pattern.

17. The program of claim 14, further comprising a code segment for applying a translation to actuators associated with the first end effector at the second location or orientation, wherein the translation is based on the best alignment position A, thereby improving starting position accuracy of the second location or orientation.

18. The program of claim 14, wherein at least one of the best alignment position A and the best alignment position B are calculated as a center of mass type equation or based on a weighted average of signal strengths.

19. An ultrasonic inspection system for ultrasonic inspection of a part, the system comprising:
a first end effector having at least one transducer configured to transmit or receive ultrasonic or sound waves through the part; and
a second end effector having at least one transducer configured to transmit or receive ultrasonic or sound waves through the part;
actuators configured to receive commands for actuating the first end effector and the second end effector; and
a system controller comprising a processor configured for determining alignment calibration data for at least one of the first end effector and the second end effector while the first and second end effectors are located on opposite sides of the part, and configured for outputting command signals to the actuators for actuating the at least one of the first end effector and the second end effector according to the determined alignment calibration data,
wherein the system controller is further configured for sending signals to one of the actuators to actuate the first end effector according to a first scanning pattern within a predetermined work envelope, starting at a first location or orientation, while the first end effector transmits or receives ultrasonic or sound waves and the second end effector receives or transmits ultrasonic sound waves at each point along the first scanning pattern,
wherein the system controller is further configured to start a second scanning pattern:
at a current location or orientation if a current signal sent or received by the first end effector at the current location is greater than a threshold amount more than a previous signal sent or received at a previous location or orientation,
at a location or orientation along the first scanning pattern at which signal strength received or sent by the second end effector was strongest, or
at the current location or orientation if the current signal sent or received by the first end effector at the current location exceeds a threshold signal strength.

20. The system of claim 19, wherein the second scanning pattern runs at a lower speed, makes tighter turns, or runs at a higher resolution than the first scanning pattern.

* * * * *